United States Patent [19]
Hacker

[11] 3,970,388
[45] July 20, 1976

[54] LIQUID STOPPED-FLOW APPARATUS

[76] Inventor: Charles L. Hacker, 2697 Parman Road, Dansville, Mich. 48819

[22] Filed: July 15, 1974

[21] Appl. No.: 488,567

[52] U.S. Cl. .................................. 356/72; 356/201; 23/253 R; 356/246
[51] Int. Cl.² ......................................... G01N 21/00
[58] Field of Search ............ 356/72, 180, 181, 201, 356/208, 246, 39, 40; 250/573–576; 23/253 R

[56] References Cited
UNITED STATES PATENTS

| | | | |
|---|---|---|---|
| 2,254,782 | 9/1941 | Riche | 356/208 |
| 3,527,570 | 9/1970 | Penhasi | 23/253 R |
| 3,622,795 | 11/1971 | Dorman et al. | 250/576 |
| 3,635,564 | 1/1972 | Zuckerman et al. | 356/72 |
| 3,705,773 | 12/1972 | Vicario | 356/180 |
| 3,874,850 | 4/1975 | Sorenson et al. | 356/40 |

Primary Examiner—Vincent P. McGraw
Assistant Examiner—Jon W. Henry
Attorney, Agent, or Firm—Beaman & Beaman

[57] ABSTRACT

Apparatus for evaluating the characteristics of mixed fluids while under a static or "stopped-flow" condition. Fluid injector pistons force the fluids to be mixed into a mixing chamber, and from the mixing chamber the fluids enter an evaluation or test cell. An amount of mixed fluid in excess of that required to occupy the evaluation cell is introduced into the cell with the excess fluid being exhausted from the cell into an accumulator which maintains a pressurized fluid state. The evaluation cell includes quartz windows permitting light to pass through the cell after flow of the mixed fluid ceases after termination of the fluid injection, and the evaluation cell may also include electrodes to permit both light transmitting characteristics and electrical characteristics of the mixed fluid to be tested. The subsequent cycle of operation purges the cell of the previously mixed fluid permitting a fresh mixture to be introduced into the cell for testing and evaluation. Injection of the fluids into the mixing chamber may be produced with a combination electrical-mechanical drive mechanism, or may be produced by a pressurized fluid, such as compressed air.

5 Claims, 10 Drawing Figures

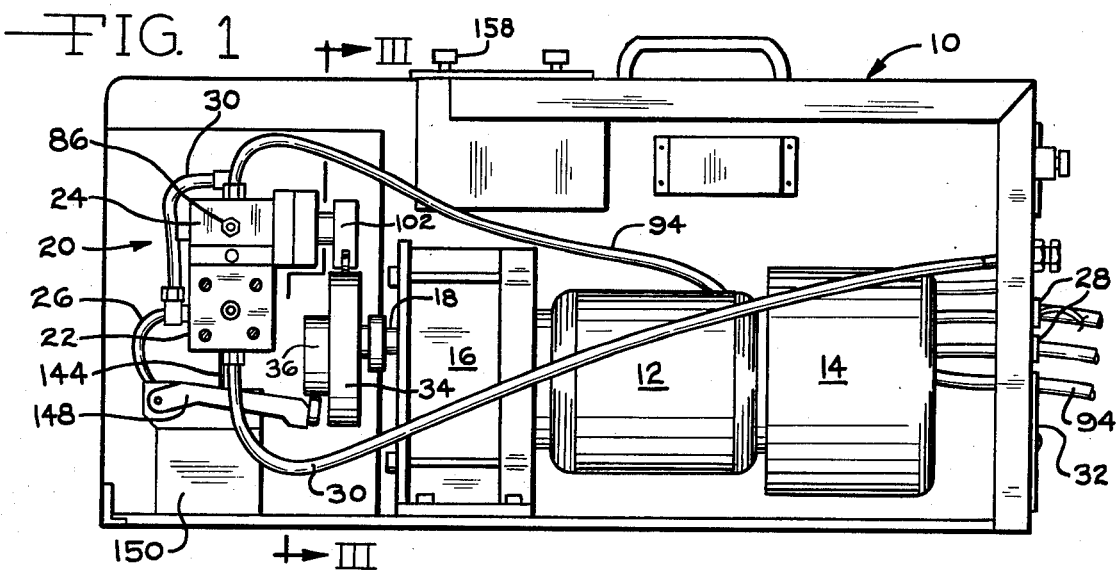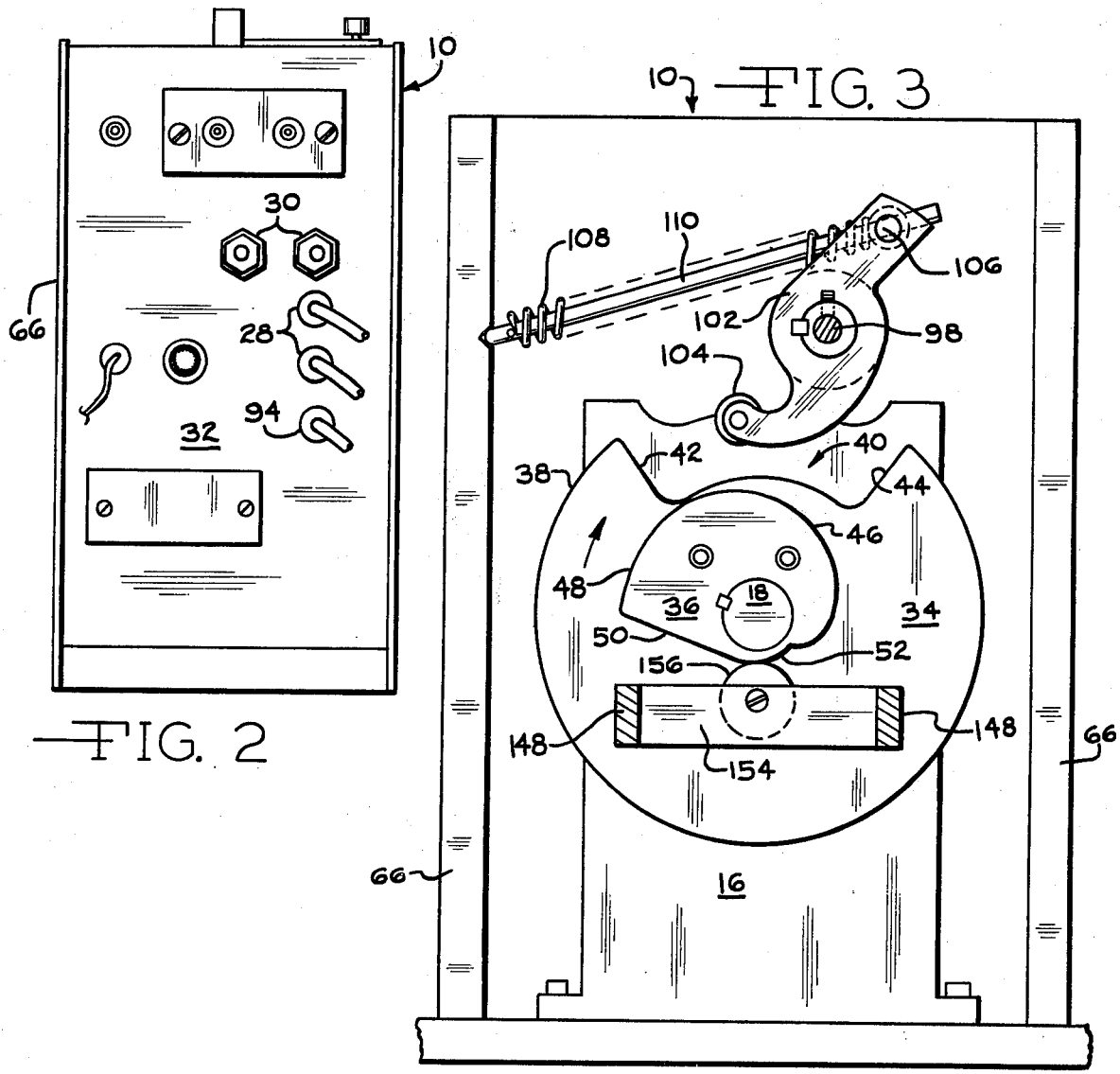

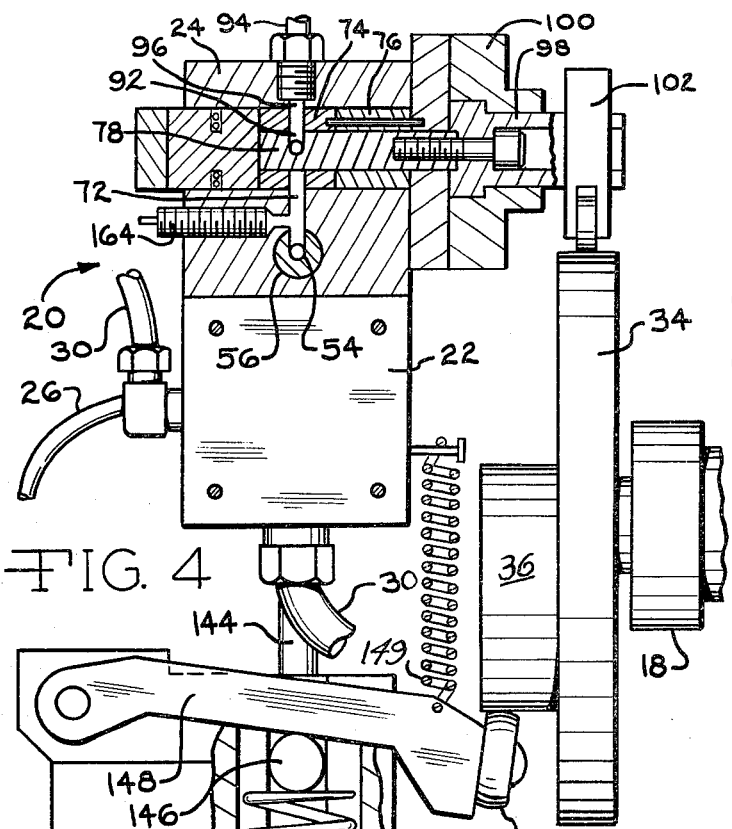

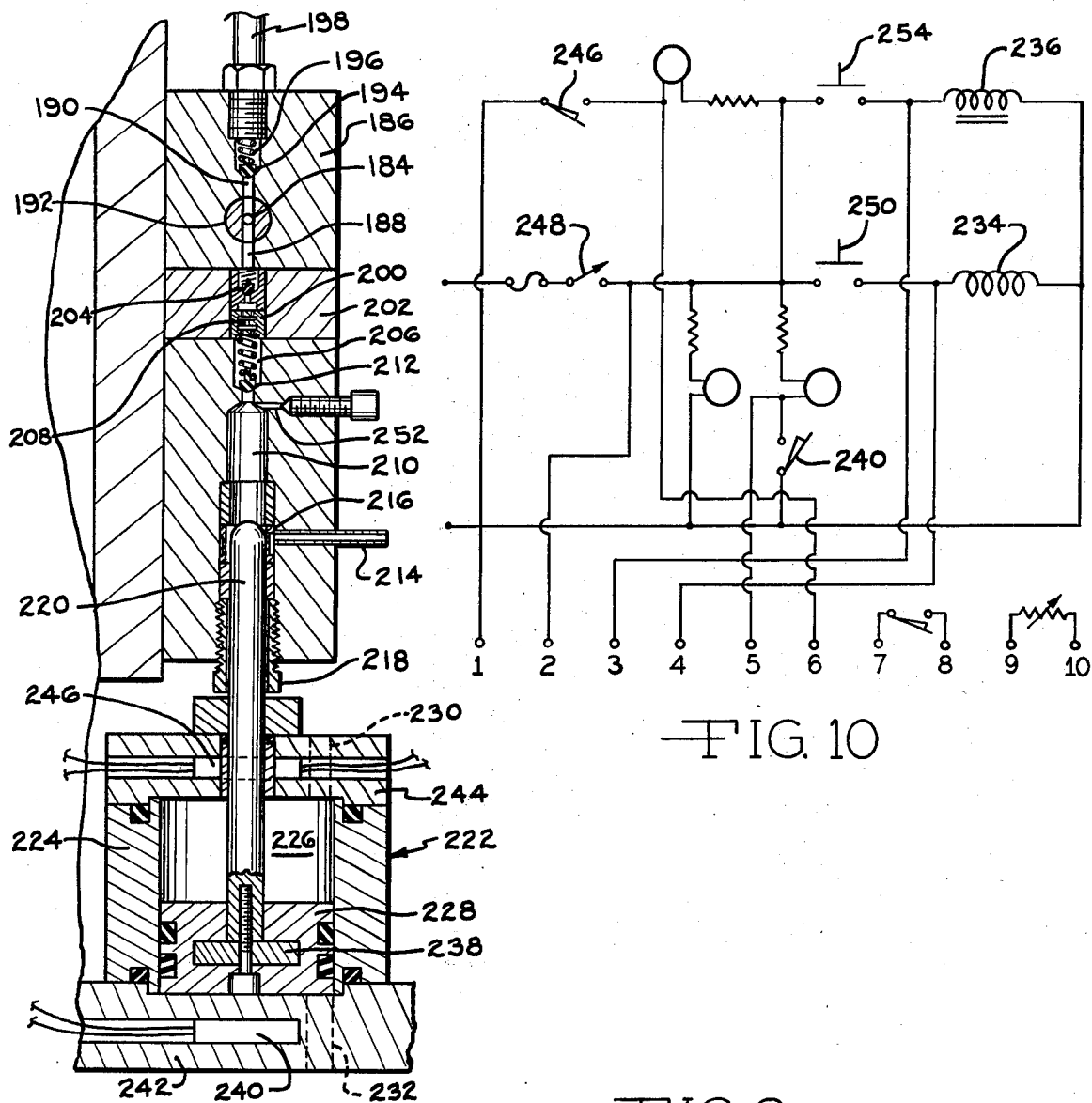
FIG. 8
FIG. 10
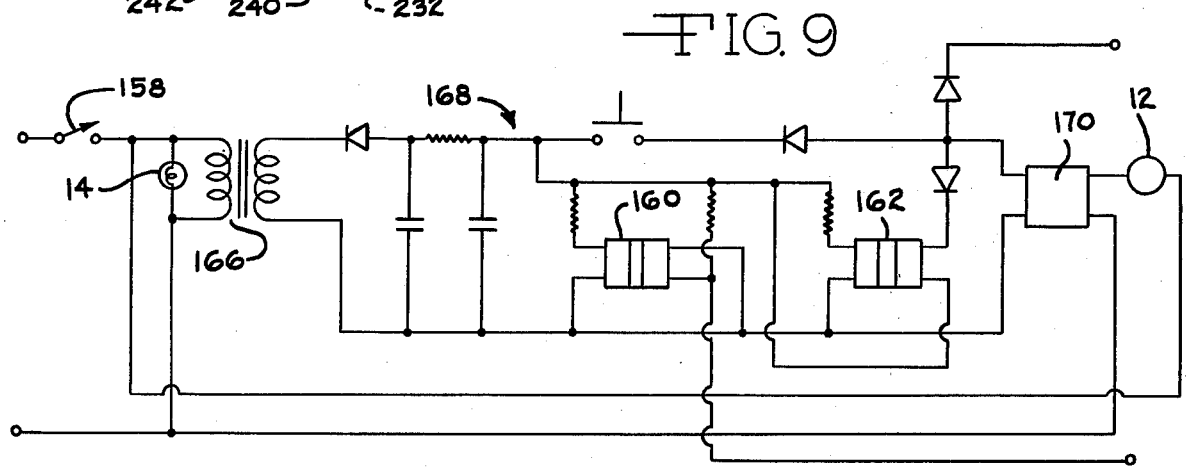
FIG. 9

LIQUID STOPPED-FLOW APPARATUS

BACKGROUND OF THE INVENTION

The invention pertains to fluid testing and evaluating apparatus for evaluating mixtures of fluids, usually liquids, under static conditions.

Among the many types of tests conducted upon fluids, particularly liquids, is the observing and evaluation of fluid mixtures immediately after mixing, and under static conditions. Such testing permits an evaluation of the separation and combining of dissimilar molecules, the observing of interaction of the fluid particles, the determination of the compatibility and completeness of mixing of the fluids, the observation of the type and completeness of chemical reaction, and the testing of variations in electrical characteristics of the mixture and other similar effects can be evaluated by using stopped-flow apparatus.

Fluid analyzing is known wherein fluid mixtures may be observed while in the static state as typified by U.S. Pat. Nos. 3,705,771 and 3,713,743. Also, it is known to inject a fluid into a test chamber during testing and analysis as shown in U.S. Pat. No. 3,764,894. However, known static fluid testing apparatus for evaluating fluid mixtures is expensive and cumbersome, and stopped-flow fluid mixture testing apparatus which could be used in small laboratories and testing facilities, and is economically feasible for small testing facilities, has not heretofore been available.

SUMMARY OF THE INVENTION

It is an object of the invention to provide stopped-flow fluid mixture testing apparatus which is of a relatively economical construction, concise size and ease of operation as to make such apparatus available on a much wider basis than theretofore possible.

Further, an additional object of the invention is to produce a stopped-flow fluid mixture testing apparatus which is capable of uniformly and thoroughly mixing separate fluids immediately prior to introduction of the mixture into an evaluation cell wherein the characteristics of the mixture may be evaluated immediately after mixing.

An additional object of the invention is to provide a stopped-flow fluid mixing apparatus wherein the testing cell is purged during each cycle to prevent inaccurate testing results due to a dilution of sequential mixtures.

Another advantage of the invention lies in the ability of the apparatus to maintain the fluid mixture under a positive pressure while in a static condition so as to minimize the formation of gas bubbles and voids.

Another object of the invention is to provide a stopped-flow fluid mixing testing apparatus which is capable of being electrically operated, and is able to maintain uniform temperature and pressure conditions of the fluids during mixing and evaluation.

In the practice of the invention the fluids to be mixed, two in number, in the described embodiments, are drawn into expansible chambers by pistons. The fluids within the chambers are simultaneously forced into a mixing chamber, and the mixed fluids immediately pass into the testing and evaluating cell. An amount of fluid is mixed and injected into the cell greater than that necessary to fill the cell whereby excess fluid mixture flows from the cell into an accumulator which is part of the cell exhaust system. Thus, the initial fluid mixture introduced into the cell serves to purge the cell of the previously tested mixture.

The fluid flow through the cell terminates upon cessation of movement of the injector pistons, and quartz windows within the cell permit light to pass through the cell for optical and light testing purposes. The cell may also include electrodes and other testing apparatus for evaluating other physical characteristics of the fluid mixture within the cell while under a static condition.

The injector pistons may be actuated by an electric motor and mechanical drive means, which includes cams and springs; or the pistons, as in the disclosed variation, may be operated by a pressurized fluid medium, such as compressed air. Control means are utilized to synchronize the operations of the apparatus, and in the electrical-mechanical embodiment a rotating valve communicating with the accumulator and testing cell outlet permits operation of the injector pistons upon exhausting of the accumulator.

The fluid system of the apparatus includes check valves, and other control components, which permit a new charge of fluid to be introduced into each injector chamber as the associated pistons are reversed in direction and the testing apparatus may quickly cycle through subsequent testing cycles.

BRIEF DESCRIPTION OF THE DRAWINGS

The aforementioned objects and advantages of the invention will be appreciated from the following description and accompanying drawings wherein:

FIG. 1 is a side elevational view of stopped-flow apparatus in accord with the invention with the side panel of the housing removed, FIG. 2 is an end view of the apparatus housing as taken from the right of FIG. 1, FIG. 3 is an elevational, sectional view illustrating the cam structure as taken along section III—III of FIG. 1, FIG. 4 is a detail, elevational, partially sectioned side view of the test cell structure and injector piston operating mechanism as taken along section IV—IV of FIG. 5 with the valve rotated 90°.

FIG. 5 is an enlarged, detail, elevational, cross-sectional view of the test cell and fluid injector head, FIG. 6 is an enlarged, detail, sectional view of the mixing chamber and adjacent structure, FIG. 7 is an enlarged, detail, sectional view of a testing cell in accord with the invention having electrodes located therein, FIG. 8 is an elevational, sectional view of another embodiment of the invention utilizing an expansible motor to operate the injector pistons, FIG. 9 is an electrical circuit diagram of the embodiment of FIGS. 1 through 6, and, FIG. 10 is a circuit diagram of the circuitry used with the expansible motor operated embodiment of FIG. 8.

DESCRIPTION OF THE PREFERRED EMBODIMENTS

The preferred embodiment of the invention is the electric motor driven embodiment illustrated in FIGS. 1 through 6. The overall relationship of components of a stopped-flow apparatus in accord with this embodiment will be appreciated from FIG. 1.

The apparatus is enclosed within a rectangular cabinet or housing generally indicated at 10 having a carrier handle. In FIG. 1 the left side panel of the housing is removed to display the components housed therein which include an electric motor 12 having an electrical braking apparatus affixed to the drive shaft as represented at 14. The braking apparatus may be of any conventional electrical type capable of quickly stopping the rotation of the motor shaft upon deenergizing of the motor. The electric motor drives a speed reduction transmission 16, of conventional construction, having an output shaft 18 upon which the control cams are mounted, as later described.

The fluid mixture evaluating cell, and the fluid injecting apparatus, are mounted within a head 20 consisting of a lower block 22 and an upper block 24, FIG. 5. Injector piston operating apparatus which is "cocked" by one of the cams mounted upon the output shaft of transmission 16 is located below the head 20.

The head 20 is supplied with the fluids to be mixed by conduits 26, having fittings 28 defined in the end panel 32, FIG. 2. As it is desirable to maintain the temperature of the head 20 as uniform as possible at a predetermined temperature, liquid temperature control means, such as a liquid, are circulated through the head, and this temperature control fluid is supplied to the head through conduits 30. The other electrical apparatus, such as oscilloscope connections, thermocouples and the like, are also electrically accessible by mounting appropriate terminals upon the end panel 32, and the electric supply cord for the electric motor 12 passes through the panel.

The drive shaft 18 supports cams 34 and 36. The cam 34 is provided with a circular periphery 38 having a notch 40 defined therein by radially disposed edges 42 and 44. The cam 36 is of a lobe configuration having a spirally oriented surface 46 increasing from a minimum radial dimension to a maximum radial dimension at 48, an abrupt relief at 50, and a "dwell" portion 52. These cams are maintained upon the drive shaft by conventional keying means, and are fixed with respect to the shaft and each other.

The fluid mixture evaluating and testing cell structure is best appreciated from FIGS. 4 and 5. Basically, the cell 54 comprises an elongated narrow passage defined in a sleeve 56 mounted in the upper head block 24. The cell passage includes opposed and spaced ends defined by light transmitting windows 58, preferably formed of quartz. The windows 58 are maintained in a liquid tight relationship with the ends of the cell by annular threaded plugs 60 threaded into holes 62 defined in the block 24 and the plugs also maintain the cell sleeve 56 within the block. The plugs 60 are each provided with a longitudinal central passage in alignment with the cell 54, and it will be appreciated that this structure permits light to pass longitudinally through the cell, and as the quartz windows 58 are firmly mounted in the block the fluid within the cell may be maintained under a high pressure, if desired. Tubular light seals 64 are interposed between the head 24 and housing sides 66 in alignment with the cell and the housing observation ports 68 insuring that no ambient light will enter the cell or its readout.

The cell 54 and sleeve 56 are provided with an inlet 70 adjacent the left end, FIG. 5, and an outlet 72 adjacent the right end. The outlet passage 72 defined in the block 24 intersects the cylindrical valve sleeve 74 defined in the block within bore 76. The two-part valve sleeve 74 serves to rotatably support the rotary valve 78. An accumulator chamber 80 is defined in the block 24 having a passage 82 in communication with the valve sleeve, and the accumulator includes a piston 84 slidably mounted within the threaded head 86 biased to the left under the influence of compression spring 88. When the piston 84 is moved to the right the outer end of the piston rod 90 will extend from the threaded head 86.

The rotary valve 78 includes a right angled passage 92 selectively establishing communication between cell outlet passage 72 and accumulator 80 when the valve is in the rotary position of FIG. 5. A 90° counterclockwise rotation of the valve 78 establishes communication between the accumulator 80 and the fluid mixture drain line 94 through head passage 96. Thus, the accumlator will empty itself of fluid mixture upon communication with the drain line 94 under the influence of the spring 88.

The rotary valve 78 is operated by the concentric shaft 98 journaled in bearings 100. The lever 102 is mounted on shaft 98 and includes a cam roller 104 and a spring guide rod anchor 106. As viewed in FIG. 3, the valve shaft 98 is biased in the clockwise direction by a compression spring 108 mounted upon a guide rod 110 engaging the left housing side 66. The lever 102 is in alignment with the cam 34, and in the position of FIG. 3, the cam roller 104 is within notch 40 between edges 42 and 44 such that clockwise rotation of the cam 34 will cause the roller 104 to be engaged by edge 42 pivoting the valve shaft 78 in a counterclockwise direction until the roller rides upon the cam periphery 38.

Introduction of the mixed fluid into the cell 54 is accomplished by a pair of injector cylinders and pistons located within the head block 22, FIG. 5. As appreciated from FIG. 5, and FIG. 6, a mixing chamber 112 is defined in the block 22, adjacent the intersection of the block, and adjacent the left end of the cell 54 communicating with the cell inlet 70. The mixing chamber includes a mixing element 114 provided with annular grooves 116 and axially extending passages 118 interconnecting the annular grooves whereby the fluids may be thoroughly mixed prior to entering the cell 54. The mixing element is recessed at its lower region to form lower groove 116 for initially receiving the fluids to be mixed, and these fluids are introduced into the mixing chamber through injector cylinder outlet passages 120, FIG. 6. The outlet passages 120 each include an enlarged portion defining an annular valve seat 122 which cooperates with an axially movable check valve 124. The check valves 124 are each provided with a plurality of axially extending passages 126 at their peripheries whereby fluid flowing from the injector cylinder may unseat the check valve and flow around the check valve through the passages 126 into the mixing chamber 112. The check valves 124 are biased toward their closed position by compression springs 128 received within recesses defined in the check valves and in the mixing element 114.

A pair of identical injector cylinders 130 are formed in the head block 22 communicating with the outlet passages 120. The cylinders are of a stepped diameter including a reduced diameter and a larger threaded portion. Each cylinder includes an annular synthetic plastic sleeve liner 132, and an annular fluid inlet port ring 134 provided with radial passages in axial alignment with the fluid inlet ports 136, FIG. 6. Sleeves 138 seal the port rings and the entire cylinder assembly is maintained by threaded glands 140. A longitudinally movable piston 142 reciprocates within the glands 140 and the cylinders 150 for drawing fluid into the cylinders, and injecting the fluid from the cylinders into the mixing chamber and cell.

The pistons 142 are simultaneously reciprocated by a linear drive means which includes a pushrod 144, FIG. 4, mounting a crossbar 146 engaging the underside of the two arms of "cocking" lever 148 pivotally mounted upon base 150. The base 150 is located directly below the head 20, and compression spring 152 engages the underside of the crossbar 146 for biasing the pushrod 144 upwardly to permit the pistons to enter the cylinders 130 and inject the fluid into the mixing chamber.

The outer end of the cocking lever 148 is provided with a portion 154 supporting the cam engageable roller 156, FIGS. 3 and 4, in alignment with the cam 36 for engagement with the cam periphery, and the lever 148 is biased upwardly by spring 149.

As it is desirable that test conditions be made as uniform as possible the temperature of the fluid within the cell 54 is closely regulated, and this temperature control is accomplished through the circulation of a controlled temperature fluid pumped through the head blocks 22 and 24. The temperature controlling fluid is provided to the blocks via conduits 30 and removed from the blocks through suitable exhaust conduits. The circulation of a temperature control fluid through the head blocks will maintain the head at the desired temperature, and also maintain the fluids being tested at a uniform temperature to provide a comparative basis for evaluation.

The control circuitry for the described testing apparatus is shown in FIG. 9. This circuitry includes start switch 158 for electric motor 12, motor braking coil 14 and position sensors 160 and 162, which in the commercial form of the invention are light emitting diodes and light sensitive receivers. The sensor 160 senses the rotary position of the cam 34, and the other sensor 162 is so positioned as to sense whether or not the accumulator piston rod 90 is projecting from the head 86. These sensors can be of any conventional form, such as photo cells, switches, magnetic devices, or the like, and are positioned in any conventional manner to function as described.

The transformer 166 energizes the low voltage control circuit 168, which includes the sensors and relay 170 and diodes, condensers and resistors to provide the desired electrical characteristics.

In use, the fluid supply ports 136 are connected to the fluids to be mixed by conduits 26, the drainage conduit 94 is attached to a drain or reservoir, and the temperature control conduits 30 are attached to temperature controlled fluid circulating means of any conventional type. Initially, the apparatus is usually primed through a port closed by screw 164 and run through several cycles before testing is initiated in order to fully charge the system with fluid so that subsequent operating cycles will be uniform in volume and fluid flow characteristics.

Initially, the rotary valve 78 is biased to the position of FIG. 3 as the cam follower roller 156 is located between the cam notch edges. In this position the valve passage 92 establishes communication between the cell outlet passage 72 and the accumulator 80, as shown in FIG. 5. When the electric motor 12 is started by switch 158 to close relay 170, the cams 34 and 36 begin to rotate in a clockwise direction as indicated by the arrow in FIG. 3 causing the cam edge 42 to engage the roller 104 and begin pivoting the valve in the counter-clockwise direction, and causing the cam roller 156 to roll along the spiral surface of cam 36. As the motor starts, the sensor 160 is operated to produce a holding current at the relay 170 and to avoid interference from the other portions of the circuit all inputs to the relay are gated by diodes. As cam rotation continues the roller 104 will engage the cam periphery 38, establishing communication between the accumulator 80 and the drainage conduit 94 via valve passage 92, permitting the fluid within the accumulator to be exhausted through the valve 78 and drainage conduit under the force of the spring 88. The accumulator piston 84 will then be located at its leftmost position as shown in FIG. 5.

As the cams continue to rotate, the cam follower 104 traverses the cam periphery 38 maintaining the cell outlet passage 72 closed, and as the cam roller 156 traverses the cam surface 46 the lever 48 is biased downwardly, FIG. 4, forcing the crossbar 146 downwardly, and the spring 152 will be compressed as the piston pushrod is lowered. As the pushrod is lowered the pistons 142 move downwardly within the cylinders 130 creating a vacuum within the cylinders as check valves 124 prevent entry of fluid into the cylinders, and the fluid supply conduits cannot communicate with the cylinders until the ports 136 are opened when the pistons reach their lower range of movement. Upon this lower range being reached, and the ports 136 are uncovered, the fluid to be tested will enter the cylinders 130, and this occurrence takes place when the cam roller 156 is located at the maximum diameter 48 of the cam.

At this point the components will be as illustrated in FIG. 5, except the valve 78 will be rotated 90° counterclockwise from that shown which closes the cell outlet passage 72.

After the injector cylinders have been filled with the fluid to be mixed, the cam roller 156 "falls" from the cam periphery 48 due to the roller passing over relief 50 and the cocking lever roller 156 will be maintained in engagement with the cam 36 by spring 149, and the pistons 142 will be held in their lowermost position due to the fact that the cylinders 130, mixing chamber 112, cell 54 and outlet passage 72 are filled with fluid, and the fact that the fluid cannot flow from the cell outlet passage 72 will hold the pistons 142 in the "cocked" position. This delay under pressure allows the fluid within cylinder 130 to reabsorb any gases that may have been lost during charging.

As soon as cam roller 104 passes over edge 44 and falls into the cam notch 40, the valve 78 is very rapidly rotated by the spring 108 to the position shown in FIG. 5 establishing communication between the cell outlet 72 and the accumulator 80. As the force generated by the spring 152 is significantly greater than the spring force biasing the accumulator piston 84 to the left, the spring 152 drives the pistons 142 upwardly very quickly to inject the fluid contained within the cylinders 130 into the mixing chamber 112 and into the cell 54, passage 72, valve 78 and into the accumulator 80. This action purges the mixing chamber and the cell of the mixed fluid from the previous cycle, and as the volume of the cylinders 130 is significantly greater than the volume of fluid within the mixing chamber and cell, an entire "fresh" mixture of the fluids within the cylinders 130 is introduced into the cell, while the "old" fluid mixture will be within the accumulator 80, and partially mixed with newly injected fluid which passes through the cell 54 during operation of the pistons. The charging of the accumulator 80 is sensed by the extension of the piston rod 90 from the head 86 by the adjacent sensor 162 which can signal the start of the testing cycle, and the electric motor is braked to cease rotation of the cams. As the fluids driven from the cylinders 130 were thoroughly mixed within the mixing chamber 112, the fluid mixture within the cell is ready for testing and evaluation, and testing may consist of passing a light through the observation cell 54 and manually observing the intensity thereof, or automatic optical testing procedures may be conducted on the mixture by any conventional light analyzing apparatus located on opposite sides of housing 10 in alignment with ports 68.

The fluid within the cell 54 is in a static condition, and is maintained under pressure due to the influence of the accumulator spring 88. Thus, bubbles and gas cavities within the fluid are minimized, and the fluid within the cell may be tested under uniform temperature and static conditions.

To initiate the next cycle of testing, the electric motor is energized by switch 158 which initially causes the valve 78 to be rotated counterclockwise, FIG. 5, as described above, permitting the accumulator 80 to be purged, and the cycle may be repeated. It will be appreciated that when the valve 78 is rotated to permit fluid flow from the cell outlet 72 during charging of the testing cell the upward movement of the pistons 142 raises the cocking lever 148 so that the cam roller 156 engages dwell 52 and may again engage the cam surface 48.

FIG. 7 illustrates, on an enlarged scale, a cell and cell sleeve which may be used with apparatus of the type previously described for testing electrical charcteristics of the mixing fluid, as well as providing optical testing.

In the cell of FIG. 7, the cell sleeve 172 is substituted for that shown in FIG. 5, and this cell sleeve includes two pair of electrodes 174 and 176 which communicate with the cell bore 178. The electrodes of a pair are separated by a dielectric material 180, and the sleeves 182 are also formed of a dielectric material whereby the only electrical connection between the electrodes will be the fluid mixture within the cell bore. The electrodes are connected by conductors, not shown, to which the test instrumentation is attached, and the electrodes of a pair may be used during a test, both pairs of electrodes may be simultaneously employed, or two electrodes of separate pairs used which are spaced at a significant distance from each other.

The cell of FIG. 7 is also used in conjunction with the quartz windows 58, and light and optical testing of the mixed fluid within the cell may simultaneously occur during the testing of the electrical characteristics of the mixture.

A variation of apparatus using the inventive concepts is disclosed in FIGS. 8 and 10, and for purpose of simplification only a single injector cylinder is shown. In this embodiment the cell 184 is defined in block 186, and comprises a horizontally disposed passage within sleeve 192 having an inlet passage 188 and an outlet passage 190 located at the opposite end, as in the previously described embodiment. Also, the cell 184 is provided with quartz windows at its opposite ends, and may be of a construction identical to that shown in FIG. 5. The outlet passage 190 communicates with the check valve 194 biased into a closed relationship with its seat by compression spring 196 whereby fluid passing the check valve enters the drainage conduit 198.

The mixing chamber 200 is defined in block 202 and communicates with the inlet passage 188. The mixing chamber is sealed by a spring biased check valve 204, and a premix chamber 206 including a plurality of mixing passages 208 communicates with the mixing chamber.

The injector devices, two being used in the preferred embodiment, but only one being shown for purpose of illustration, each include a cylinder 210 having guide sleeves of synthetic plastic material, and communicate with the premix chamber 206 through spring biased check valves 212. Both injector cylinders 210 communicate with the chamber 206 through check valves 212, and each cylinder communicates with a fluid supply through a conduit 214 communicating with the annular port ring 216, as previously described. The annular gland 218 maintains the ejector cylinder assembly whereby a sealed relationship between the cylinder 210 and the piston 220 is achieved.

The pistons 220 are reciprocated within their associated cylinder by an expansible motor 222, preferably of the compressed air operated type. Expansible motor 222 includes a cylinder body 224 defining a chamber 226 in which the piston 228 reciprocates. Ports 230 and 232 communicate with the opposite ends of the chamber 226 for biasing the piston upwardly and downwardly, and solenoid valves 234 and 236, FIG. 10, control the flow of air through the ports 230 and 232 through conduits, not shown.

For control purposes, the position of the piston 228 is sensed by locating a permanent magnet 238 within the piston, and a reed switch 240 is located in the head 242. When the piston 228 is in its lowermost position, as illustrated, the magnet 238 will close the contacts of the reed switch 240. When the piston 228 is in its uppermost position, engaging head 244, the magnet 238 will no longer influence the reed switch 240, but will close the contacts of the reed switch 246.

The sequence of operation of the embodiment of FIG. 8 is very similar to that of the previously described embodiment. Switch 248 is closed to engage the circuit. To charge the cylinders 210 with the fluid to be mixed switch 250 is closed to open valve 234 and compressed air is supplied to the expansible motor through conduit 230 to lower the piston 228 and pistons 220. Initially, fluid may be introduced into the cylinders 210 through the priming passage 252. When the cylinders 210 are filled with the fluid to be mixed, switch 254, FIG. 10, is closed energizing valve 236 to introduce compressed air into the chamber 226 through port 232 quickly driving the pistons 220 upwardly, and forcing the fluid within the cylinders 210 into the chamber 206, through the mixing chamber 200, and into the testing cell passage 184. As the amount of mixed fluid forced into the testing cell is considerably greater than that necessary to fill the cell the excess fluid is forced past the check valve 194 into the drainage conduit 198. Termination of movement of the pistons 220 produces a static condition of the mixed fluid within the cell 184 and testing and evaluation of the mixture may now take place.

To recharge the cell with a new mixture the piston 228 is lowered, creating a vacuum within the cylinders 210 permitting fluid to be drawn into the cylinders upon the pistons uncovering the port ring 216. The cycle may again be repeated, and subsequent mixtures of fluid quickly tested and evaluated. The circuit includes indicator lights to indicate the position of the piston 228 as controlled by the reed switches.

While the embodiment of FIG. 8 is somewhat simpler than the embodiment of FIGS. 1 through 6, this embodiment requires the presence of compressed air, and cannot produce the rapidity of mixing achieved with the previously described embodiment. As the embodiment of FIGS. 1 through 6 is electrically operated by 110 volts, it may be readily utilized at all testing facilities without requiring the presence of compressed air, and the sequence of operation produces a very quick mixing of the fluids and an effective purging of the system during each cycle.

It will be appreciated that the described embodiments of the inventive concept achieve the desired objectives and advantages, and it is to be understood that various modifications may be apparent to those skilled in the art without departing from the spirit and scope of the invention.

I claim:

1. Apparatus for rapidly mixing fluids for evaluating the mixture while in a static condition comprising, in combination, an evaluation cell having an inlet and an outlet, fluid evaluation means directly associated with said cell, a fluid mixing chamber communicating with said cell inlet, a pair of injector chambers each having an inlet and an outlet and a piston slidably located therein, said chamber's outlets communicating with said mixing chamber and said inlets communicating with fluid supply means, a compression spring drivingly connected to said pistons for biasing said pistons into its associated injector chamber to force fluid therein into said mixing chamber and cell, an electric motor having a rotatable output drive shaft, a first cam mounted upon said drive shaft, a first cam follower engageable by said cam compressing said spring during partial rotation of said drive shaft, a valve within said cell outlet controlling exhausting of said cell, a second cam mounted upon said drive shaft, a second cam follower engaging said second cam controlling operation of said valve opening said valve after compression of said spring whereby opening of said valves causes said pistons to inject fluid into said mixing chamber and cell.

2. In a fluid mixing apparatus as in claim 1 wherein said fluid evaluation means includes light transmitting window means defined in said cell.

3. In a fluid mixing apparatus as in claim 2 wherein said fluid evaluation means includes a pair of spaced electrodes within said cell.

4. In a fluid mixing apparatus as in claim 2 wherein said cell comprises an elongated chamber having spaced opposed ends, a light transmitting window being located at each of said cell ends.

5. Apparatus for rapidly mixing fluids as in claim 1, an accumulator communicating with said cell outlet, and pressure producing means within said accumulator maintaining fluid therein under pressure.

* * * * *